US007186422B2

(12) United States Patent
Jensen et al.

(10) Patent No.: US 7,186,422 B2
(45) Date of Patent: Mar. 6, 2007

(54) **PREVENTATIVE AND TREATMENT EFFECTS OF *MORINDA CITRIFOLIA* ON DIABETES AND ITS RELATED CONDITIONS**

(75) Inventors: Claude Jarakae Jensen, Cedar Hills, UT (US); Afa Kehaati Palu, Orem, UT (US); Hifumi Ohishi, Tokyo (JP); Hisanori Tani, Tokyo (JP)

(73) Assignee: Morinda, Inc., Provo, UT (US)

( * ) Notice: Subject to any disclaimer, the term of this patent is extended or adjusted under 35 U.S.C. 154(b) by 51 days.

(21) Appl. No.: 10/993,883

(22) Filed: Nov. 19, 2004

(65) Prior Publication Data

US 2005/0147700 A1 Jul. 7, 2005

Related U.S. Application Data

(62) Division of application No. 10/286,167, filed on Nov. 1, 2002, now Pat. No. 6,855,345.

(60) Provisional application No. 60/335,313, filed on Nov. 2, 2001.

(51) Int. Cl.
*A61K 36/746* (2006.01)
*A61K 36/00* (2006.01)

(52) U.S. Cl. .................................... 424/725
(58) Field of Classification Search ................ 424/725
See application file for complete search history.

(56) References Cited

OTHER PUBLICATIONS

Bassindale, C. Health; A Particularly Bitter Pill . . . The independent, London (UK), Jun. 11, 2000, p. 30-31 (pp. 1-3 of ProQuest).*

Better nutrition, Gentle Arthritis Help; Atlanta, GA., Sep. 2000, vol. 62, Iss. 9, p. 22, 1 page (pp. 1-2 of ProQuest direct).*
Starbuck, J. Elderberry & Cat's Claw Wisely Harnessing the Power of Herbs OFR Immune-Boosting and More; Better Nutrition, Atlanta, GA., Sep. 1998, vol. 60, Iss. 9, p. 54, 4 pages (pp. 1-5 of ProQuest).*
Sang et al.; "Chemical Components in Noni Fruits and Leaves (*Morinda citrifolia* L.)"; Quality Management of Nutraceuticals: Proceedings of a Symposium, Washington D.C., Aug. 2000, Published by : ACS, Washington D.C. 2002 pp. 134-150.
Sang et al.; "Flavonol Glycosides and Novel Iridod Glycoside from the Leaves of *Morinda citrifolia*"; Journal of Agricultural and Food Chemistry, Sep. 2001 vol. 49, No. 9, pp. 4478-4481.
Farine et al.; "Volatile Components of Ripe Fruits of *Morinda citrifolia* and Their Effects on Drosophilia"; Quality Management of Nutraceuticals; Phytochemistry, 1996, vol. 41, No. 2, pp. 433-438.

* cited by examiner

*Primary Examiner*—Patricia Leith
(74) *Attorney, Agent, or Firm*—Kirton & McConkie; Michael F. Krieger

(57) ABSTRACT

The present invention features a unique, natural formulation and method of administering the same to treat and prevent diabetes, or rather advances treatment of diabetes, by providing a naturaceutical composition or treatment formulated with one or more processed *Morinda citrifolia* products as derived from the Indian Mulberry plant. The *Morinda citrifolia* is particularly adapted to treat Type II diabetes. The *Morinda citrifolia* product is preferably a leaf extract, but may also be in the form of a juice, a puree juice, a dietary fiber, or other similar forms and is incorporated into various carriers or naturaceutical compositions suitable for in vivo treatment of a patient. The naturaceutical may also combine other food products into the naturaceutical, such as fruit juices, dietary supplements, vitamins and minerals, and others.

11 Claims, No Drawings

PREVENTATIVE AND TREATMENT EFFECTS OF *MORINDA CITRIFOLIA* ON DIABETES AND ITS RELATED CONDITIONS

RELATED APPLICATIONS

This application is a divisional of U.S. application Ser. No. 10/286,167, filed Nov. 1, 2002 now U.S. Pat. No. 6,855,345 entitled "Preventative and Treatment Effects of *Morinda citrifolia* on Diabetes and its Related Conditions," which claims priority to U.S. Provisional Application Ser No. 60/335,313, filed Nov. 2, 2001, and entitled, "Methods for Treating Conditions Related to Diabetes."

BACKGROUND

1. Field of the Invention

The present invention relates to methods and various compositions and formulations for treating and preventing diabetes and its associated symptoms and conditions. Specifically, the present invention relates to *Morinda citrifolia*-based methods and naturaceutical formulations for treating pre-existing diabetes conditions, as well as to *Morinda citrifolia*-based methods and naturaceutical formulations for inhibiting, reducing, or preventing the onset or reducing the onset potential of future or additional diabetic developments. The present invention is suited for treatment and prevention of diabetes as commonly experienced in mammals, and particularly humans.

2. Background of the Invention and Related Art

Diabetes mellitus (diabetes) is a complex chronic disease which affects a large number of people in the United States. More specifically, diabetes mellitus is a group of diseases characterized by high levels of blood glucose resulting from defects in insulin secretion, insulin action, or both. It is characterized as a progressive breakdown in normal insulin-related usage of glucose. In order to function properly, the body's use of glucose must comprise a balanced output of insulin from the pancreas to transport glucose effectively to other organs and tissues for storage. Any insulin imbalance or loss of sensitivity can cause a chronic overabundance of glucose leading to diabetes.

It is estimated that a total of 15.7 million people in the United States, approximately 5.9% of the population, have diabetes in one form or another. Of those, 10.3 million people have actually been diagnosed with diabetes, while the other speculated additional 5.4 million people have gone undiagnosed.

Diabetes can be associated with serious complications and premature death. Studies have found that death rates can be twice as high among middle aged people with diabetes as opposed to those who are not suffering from the disease. Moreover, in 1996 diabetes contributed to over 193,000 deaths and was the seventh leading cause of death listed on U.S. death certificates in that same year. This is an alarming statistic considering that diabetes is believed to be under reported both as a condition and as a cause of death.

Diabetes is particularly prevalent among adults. Approximately 6.3 million people over the age of 65 (18.4% of all people in that age group) have diabetes. It is estimated that 8.2% of all adults over the age of 20 have diabetes. A smaller percentage, but nevertheless a significant number of children under the age of 20 in the United States have diabetes (0.16%).

Diabetes is equally likely to strike men as women. However, certain racial and ethnic groups are more likely to be susceptible to diabetes. For example, Mexican Americans are nearly twice as likely to have diabetes as non-Hispanic whites of a similar age as are Hispanics/Latino Americans. American Indians and Alaskan Natives are nearly three times as likely to be diagnosed with diabetes as non-Hispanic whites. Some Asian American also show an increased risk for diabetes. In some circumstances these minority groups are less likely to have access to treatments to help prevent the serious conditions that can arise as a result of diabetes because of their lack of access to health care and prescription medicines.

It is estimated that about 798,000 Americans will be diagnosed with diabetes this year alone. The estimated cost of treatment totals 98 million annually in the US. This problem is compounded by the fact that adult-onset diabetes is increasing at an alarming rate and also striking at younger ages. According to CDC statistics, in 1990–1998 diabetes increased by 33% with a 76% increase among 30–39 years old. Type II diabetes (discussed below) rarely struck before age 40 years of age or older. However, this type of diabetes is showing up in young adults and even children. The disease often causes permanent damage to younger victims before they are diagnosed.

There are several types of diabetes. Diabetes Type I develops in young children and is usually caused by the body's inability to produce insulin. Type I diabetes was previously called insulin-dependent diabetes mellitus (IDDM) or juvenile-onset diabetes. According to the CDC, Type I diabetes may account for 5% to 10% of all diagnosed cases of diabetes. Risk factors are less well defined for Type I diabetes than for type 2 diabetes, but autoimmune, genetic, and environmental factors are involved in the development of this type of diabetes Diabetes Type II develops later in life, usually as organs & tissues lose their ability to respond effectively to insulin. Type II diabetes was previously called non-insulin dependent diabetes mellitus (NIDDM) or adult-onset diabetes. The CDC estimates Type II diabetes may account for about 90% to 95% of all diagnosed cases of diabetes. Risk factors for Type II diabetes include older age, obesity, family history of diabetes, prior history of gestational diabetes, impaired glucose tolerance, physical inactivity, and race/ethnicity. As was mentioned above, African Americans, Hispanic/Latino Americans, American Indians, and some Asian Americans and Pacific Islanders are at particularly high risk for Type II diabetes.

Gestational diabetes is a third type of diabetes that develops in small but significant percentage of all pregnancies and usually ends with the pregnancy. A small percentage of diabetes may also result from specific genetic syndromes, surgery, drugs, malnutrition, infections, and other illnesses.

The chronic overabundance of glucose associated with this condition damages the body's blood vessels and leads to breakdown of body organs and ultimately death. Either form of diabetes is a disease with serious and deleterious health consequences. If left untreated diabetes can cause retinal degeneration and blindness, kidney and nerve damage, and can contribute to atherosclerosis. In extreme cases diabetes can result in the amputation of limbs and death.

The harmful consequences are not just possibilities but painful realities form many Americans who do not get the treatments they need in time. Again, according to CDC, 12,000–24,000 Americans lose their sight to diabetes each year and approximately 27,900 have kidney failure associated with the condition. Over 55,000 diabetic related ampu tations are performed each year. Diabetics are two to four times likely to suffer from heart disease, two to four times more likely to have a stroke, and three times more likely to die of complications of flu and pneumonia than non-diabetics.

Other conditions related to diabetes reported by the CDC include: nervous system diseases, which often includes impaired sensation or pain in the feet or hands, slowed digestion of food in the stomach, carpal tunnel syndrome, and other nerve problems, periodontal disease, which is a type of gum disease that can lead to tooth loss, complications of pregnancy, including congenital malformations and death of the fetus, and other complications such as diabetic ketoacidosis and hyperosmolar nonketotic coma.

Medical professionals apply three strategies for treating diabetes. First, reduce glucose absorption, which can be accomplished through with a disciplined diet. Second, reduce glucose synthesis in the liver. Third, accelerate glucose metabolism. Ideally, the most effective treatment will be able to utilize all of the treatments of type I diabetes. However, lack of insulin production by the pancreas makes Type I diabetes particularly difficult to control. Treatment requires a strict regimen that typically includes a carefully calculated diet, planned physical activity, home blood glucose testing several times a day, and multiple daily insulin injections.

Pharmaceuticals play a major role in the treatment of diabetes. Medications, such as Glycosidase inhibitors (Glucobai), Amylase, Glibenclamide, and Niacinamide are effective control drugs. Treatment of Type 1 diabetes functions to maintain blood glucose at near normal levels, and may require home blood glucose testing and multiple daily insulin injections. Treatment of Type 2 diabetes typically may include diet modification and home blood glucose testing, as well as oral medication. Unfortunately, the side effects of these drugs can be unpleasant and distressing. Side effects include hypoglycemia, upset stomach, skin rash or itching, weight gain, kidney problems, fatigue, dizzy spells, gloating and diarrhea.

Accordingly, it would be advantageous to provide a safe, over-the-counter formulation to treat diabetes and to augment or to even replace existing treatments and formulations for diabetes.

SUMMARY AND OBJECTS OF THE INVENTION

The present invention provides persons with diabetes the opportunity to safely and conveniently take measures to reduce the likelihood of contracting diabetes, as well as the opportunity to safely treat existing diabetes conditions using a natural formulation and method of treatment.

Therefore, it is an object of some embodiments of the present invention to provide a naturaceutical formulation for treating diabetes and its related conditions.

It is another object of some embodiments of the present invention to provide a naturaceutical formulation comprising one or more processed *Morinda citrifolia* products that function as the active ingredient in the naturaceutical formulation.

It is still another object of some embodiments of the present invention to balance the output of insulin to regulate and maintain proper blood glucose levels.

It is a further object of some embodiments of the present invention to provide various methods and formulations for treatment of diabetes comprising the administration of a processed *Morinda citrifolia* product embodied in one form or another.

In accordance with foregoing objects, and in accordance with the invention as embodied and broadly described herein, the present invention features a naturaceutical formulation designed to treat diabetes and its associated or related conditions and symptoms, as well as to balance and normalize insulin output and subsequent glucose transfer and to help maintain these to be within proper ranges.

The naturaceutical formulation or composition comprises, as an active ingredient, one or more processed *Morinda citrifolia* products as derived from the Indian Mulberry plant and manufactured and embodied as taught herein. The naturaceutical may also comprise other ingredients, such as food or dietary supplements, water, etc.

The processed *Morinda citrifolia* products comprise one of a processed *Morinda citrifolia* leaf hot water extract, a processed *Morinda citrifolia* leaf ethanol extract, a processed *Morinda citrifolia* leaf steam distilled extract, a processed *Morinda citrifolia* fruit juice or fruit juice concentrate, a processed *Morinda citrifolia* puree juice or puree juice concentrate, a processed *Morinda citrifolia* dietary fiber, a processed *Morinda citrifolia* oil or oil extract and a processed *Morinda citrifolia* leaf extract. The naturaceutical formulation may further comprise other ingredients, such as carrier mediums, water, other fruit juices, etc., and may be in the form of a liquid, a gel, a capsule, a tablet, a concentrate solution, a powder, or any other type of food product. In addition, the processed *Morinda citrifolia* product may be embodied in a formulation suitable for intravenous injection or systemic release or administration.

The present invention further features several methods of administering or introducing the naturaceutical formulation, or rather the processed *Morinda citrifolia* product no matter how embodied, into the body of a mammal, and particularly a human, for the treatment and prevention of diabetes and its related conditions, as well as for reducing the onset potential of diabetes by normalizing insulin output and glucose transfer.

In one exemplary embodiment, the present invention features a method for treating and preventing diabetes. In another exemplary embodiment, the present invention features a method for reducing the onset potential or the likelihood of contracting diabetes. In another exemplary embodiment, the present invention features a method for reducing glucose synthesis in the liver. In another exemplary embodiment, the present invention features a method for accelerating glucose metabolism. In another exemplary embodiment, the present invention features a method for inhibiting glucose absorption in the digestive tract. And finally, in another exemplary embodiment, the present invention features a method for improving overall glucose tolerance.

DETAILED DESCRIPTION OF THE PREFERRED EMBODIMENTS

It will be readily understood that the components of the present invention, as generally described herein, could be arranged and designed in a wide variety of different configurations. Thus, the following more detailed description of the embodiments of the system and method of the present invention is not intended to limit the scope of the invention, as claimed, but is merely representative of the presently preferred embodiments of the invention.

The presently preferred embodiments of the invention will be best understood by separating the description into sections, the first pertaining to a general discussion regarding *Morinda citrifolia*, including its origins, processing techniques, and health benefits, and the methods employed to produce and manufacture the processed *Morinda citrifolia* products used as key ingredients in the naturaceutical formulations described herein; and the second being a more detailed and specific discussion on the *Morinda citrifolia*-based methods and naturaceutical formulations or compositions used to treat and prevent diabetes and its associated or related symptoms and conditions, such treatment methods involving the prophylactic administration of the processed *Morinda citrifolia* products as described herein. Examples of experimental studies and the results obtained are also provided herein.

General Discussion of *Morinda Citrifolia* and the Methods Used to Produce Processed *Morinda Citrifolia* Products The Indian Mulberry or Noni plant, known scientifically as *Morinda Citrifolia* L. (*Morinda citrifolia*), is a shrub or small tree up to 10 m in height. The leaves are oppositely arranged with an elliptic to ovate form. The small white flowers are contained in a fleshy, globose, head-like cluster. The fruits are large, fleshy, and ovoid. At maturity, they are creamy-white and edible, but have an unpleasant taste and odor. The plant is native to Southeast Asia and has spread in early times to a vast area from India to eastern Polynesia. It grows randomly in the wild, and it has been cultivated in plantations and small individual growing plots. The *Morinda citrifolia* flowers are small, white, three to five lobed, tubular, fragrant, and about 1.25 cm long. The flowers develop into compound fruits composed of many small drupes fused into an ovoid, ellipsoid or roundish, lumpy body, with waxy, white, or greenish-white or yellowish, semi-translucent skin. The fruit contains "eyes" on its surface, similar to a potato. The fruit is juicy, bitter, dull-yellow or yellowish-white, and contains numerous red-brown, hard, oblong-triangular, winged 2-celled stones, each containing four seeds.

When fully ripe, the fruit has a pronounced odor like rancid cheese. Although the fruit has been eaten by several nationalities as food, the most common use of the *Morinda citrifolia* plant was as a red and yellow dye source. Recently, there has been an interest in the nutritional and health benefits of the *Morinda citrifolia* plant, further discussed below.

Because the *Morinda citrifolia* fruit is for all practical purposes inedible, the fruit must be processed in order to make it palatable for human consumption and included in food products used to treat diabetes and its related symptoms. Processed *Morinda citrifolia* fruit juice can be prepared by separating seeds and peels from the juice and pulp of a ripened *Morinda citrifolia* fruit; filtering the pulp from the juice; and packaging the juice. Alternatively, rather than packaging the juice, the juice can be immediately included as an ingredient in another food product, frozen or pasteurized. In some embodiments, the juice and pulp can be pureed into a homogenous blend to be mixed with other ingredients. Other process include freeze drying the fruit and juice. The fruit and juice can be reconstituted during production of the final juice product. Still other processes include air drying the fruit and juices, prior to being masticated.

The present invention particularly utilizes extracts from the leaves of the *Morinda citrifolia* plant, but also contemplates for use the fruit juice, the puree, and the oil from the *Morinda Citrifolia* plant. In a currently preferred process of producing *Morinda citrifolia* fruit juice, the fruit is either hand picked or picked by mechanical equipment. The fruit can be harvested when it is at least one inch (2–3 cm) and up to 12 inches (24–36 cm) in diameter. The fruit preferably has a color ranging from a dark green through a yellow-green up to a white color, and gradations of color in between. The fruit is thoroughly cleaned after harvesting and before any processing occurs.

The fruit is allowed to ripen or age from 0 to 14 days, with most fruit being held from 2 to 3 days. The fruit is ripened or aged by being placed on equipment so it does not contact the ground. It is preferably covered with a cloth or netting material during aging, but can be aged without being covered. When ready for further processing the fruit is light in color, from a light green, light yellow, white or translucent color. The fruit is inspected for spoilage or for excessively green color and hard firmness. Spoiled and hard green fruit is separated from the acceptable fruit.

The ripened and aged fruit is preferably placed in plastic lined containers for further processing and transport. The containers of aged fruit can be held from 0 to 30 days. Most fruit containers are held for 7 to 14 days before processing. The containers can optionally be stored under refrigerated conditions prior to further processing. The fruit is unpacked from the storage containers and is processed through a manual or mechanical separator. The seeds and peel are separated from the juice and pulp.

The juice and pulp can be packaged into containers for storage and transport. Alternatively, the juice and pulp can be immediately processed into a finished juice product in concentrate or dilute (such as with water or other fruit juices) form. The containers can be stored in refrigerated, frozen, or room temperature conditions.

The *Morinda citrifolia* juice and pulp are preferably blended in a homogenous blend, after which they may be mixed with other ingredients, such as flavorings, sweeteners, nutritional ingredients, botanicals, and colorings. The finished juice product is preferably heated and pasteurized at a minimum temperature of 181° F. (83° C.) or higher up to 212° F. (100° C.).

Another product manufactured is *Morinda citrifolia* puree and puree juice, in either concentrate or diluted form. Puree is essentially the pulp a separated from the seeds and is different than the fruit juice product described herein.

Each product is filled and sealed into a final container of plastic, glass, or another suitable material that can withstand the processing temperatures. The containers are maintained at the filling temperature or may be cooled rapidly and then placed in a shipping container. The shipping containers are preferably wrapped with a material and in a manner to maintain or control the temperature of the product in the final containers.

The juice and pulp may be further processed by separating the pulp from the juice through filtering equipment. The filtering equipment may include a centrifuge decanter, a screen filter with a size from 1 micron up to 2000 microns, more preferably less than 500 microns, a filter press, reverse osmosis filtration, and any other standard commercial filtration devices. The operating filter pressure preferably ranges from 0.1 psig up to about 1000 psig. The flow rate preferably ranges from 0.1 g.p.m. up to 1000 g.p.m., and more preferably between 5 and 50 g.p.m. The wet pulp is washed and filtered at least once and up to 10 times to remove any juice from the pulp. The wet pulp typically has a fiber content of 10 to 40 percent by weight. The wet pulp may be pasteurized at a temperature of 181° F. (83° C.) minimum and then packed in drums for further processing or made into a high fiber product.

Drying may further process the wet pulp. The methods of drying may include freeze-drying, drum drying, tray drying, sun drying, and spray drying. The dried *Morinda citrifolia* pulp may include a moisture content in the range from 0.1 to 15 percent by weight and more preferably from 5 to 10 percent by weight. The dried pulp preferably has a fiber content in the range from 0.1 to 30 percent by weight, and more preferably from 5 to 15 percent by weight.

The high fiber product may include wet or dry *Morinda citrifolia* pulp, supplemental fiber ingredients, water, sweeteners, flavoring agents, coloring agents, and/or nutritional ingredients. The supplemental fiber ingredients may include plant based fiber products, either commercially available or developed privately. Examples of some typical fiber products are guar gum, gum arabic, soybean fiber, oat fiber, pea fiber, fig fiber, citrus pulp sacs, hydroxymethylcellulose, cellulose, seaweed, food grade lumber or wood pulp, hemicellulose, etc. Other supplemental fiber ingredients may be derived from grains or grain products. The concentrations of these other fiber raw materials typically range from 0 up to 30 percent, by weight, and more preferably from 10 to 30 percent by weight.

Typical sweeteners may include, but are not limited to, natural sugars derived from corn, sugar beet, sugar cane, potato, tapioca, or other starch-containing sources that can be chemically or enzymatically converted to crystalline chunks, powders, and/or syrups. Also sweeteners can consist of artificial or high intensity sweeteners, some of which are aspartame, sucralose, stevia, saccharin, etc. The concentration of sweeteners may be between from 0 to 50 percent by weight, of the formula, and more preferably between about 1 and 5 percent by weight.

Typical flavors can include, but are not limited to, artificial and/or natural flavor or ingredients that contribute to palatability. The concentration of flavors may range, for example, from 0 up to 15 percent by weight, of the formula. Colors may include food grade artificial or natural coloring agents having a concentration ranging from 0 up to 10 percent by weight, of the formula.

Typical nutritional ingredients may include vitamins, minerals, trace elements, herbs, botanical extracts, bioactive chemicals and compounds at concentrations from 0 up to 10 percent by weight. Examples of vitamins one can add to the fiber composition include, but are not limited to, vitamins A, B1 through B12, C, D, E, Folic Acid, Pantothenic Acid, Biotin, etc. Examples of minerals and trace elements one can add to the fiber composition include, but are not limited to, calcium, chromium, copper, cobalt, boron, magnesium, iron, selenium, manganese, molybdenum, potassium, iodine, zinc, phosphorus, etc. Herbs and botanical extracts include, but are not limited to, alfalfa grass, bee pollen, *chlorella* powder, Dong Quai powder, Ecchinacea root, Gingko Biloba extract, Horsetail herb, Indian mulberry, Shitake mushroom, spirulina seaweed, grape seed extract, etc. Typical bioactive chemicals may include, but are not limited to, caffeine, ephedrine, L-carnitine, creatine, lycopene, etc.

The juice and pulp can be dried using a variety of methods. The juice and pulp mixture can be pasteurized or enzymatically treated prior to drying. The enzymatic process begins with heating the product to a temperature between 75° F. and 135° F. It is then treated with either a single enzyme or a combination of enzymes. These enzymes include, but are not limited to, amylase, lipase, protease, cellulase, bromelin, etc. The juice and pulp may also be dried with other ingredients, such as those described above in connection with the high fiber product. The typical nutritional profile of the dried juice and pulp is 1 to 20 percent moisture, 0.1 to 15 percent protein, 0.1 to 20 percent fiber, and the vitamin and mineral content.

The filtered juice and the water from washing the wet pulp are preferably mixed together. The filtered juice may be vacuum evaporated to a brix of 40 to 70 and a moisture of 0.1 to 80 percent, more preferably from 25 to 75 percent. The resulting concentrated *Morinda citrifolia* juice may or may not be pasteurized. For example, the juice would not be pasteurized in circumstances where the sugar content or water activity was sufficiently low enough to prevent microbial growth. It is packaged for storage, transport and/or further processing.

The processed *Morinda citrifolia* product may also exist as a dietary fiber produced from the fruit puree. Still further, the processed *Morinda citrifolia* product may also exist in oil form, such as an oil extract. The *Morinda citrifolia* oil typically includes a mixture of several different fatty acids as triglycerides, such as palmitic, stearic, oleic, and linoleic fatty acids, and other fatty acids present in lesser quantities. In addition, the oil preferably includes an antioxidant to inhibit spoilage of the oil. Conventional food grade antioxidants are preferably used.

The *Morinda citrifolia* plant is rich in natural ingredients. Those ingredients that have been discovered include: (from the leaves): alanine, anthraquinones, arginine, ascorbic acid, aspartic acid, calcium, beta-carotene, cysteine, cystine, glycine, glutamic acid, glycosides, histidine, iron, leucine, isoleucine, methionine, niacin, phenylalanine, phosphorus, proline, resins, riboflavin, serine, beta-sitosterol, thiamine, threonine, tryptophan, tyrosine, ursolic acid, and valine; (from the flowers): acacetin-7-o-beta-d(+)-glucopyranoside, 5,7-dimethyl-apigenin-4'-o-beta-d(+)-galactopyranoside, and 6,8-dimethoxy-3-methylanthraquinone-1-o-beta-rhamnosyl-glucopyranoside; (from the fruit): acetic acid, asperuloside, butanoic acid, benzoic acid, benzyl alcohol, 1-butanol, caprylic acid, decanoic acid, (E)-6-dodeceno-gamma-lactone, (Z,Z,Z)-8,11,14-eicosatrienoic acid, elaidic acid, ethyl decanoate, ethyl hexanoate, ethyl octanoate, ethyl palmitate, (Z)-6-(ethylthiomethyl)benzene, eugenol, glucose, heptanoic acid, 2-heptanone, hexanal, hexanamide, hexanedioic acid, hexanoic acid (hexoic acid), 1-hexanol, 3-hydroxy-2-butanone, lauric acid, limonene, linoleic acid, 2-methylbutanoic acid, 3-methyl-2-buten-1-ol, 3-methyl-3-buten-1-ol, methyl decanoate, methyl elaidate, methyl hexanoate, methyl 3-methylthio-propanoate, methyl octanoate, methyl oleate, methyl palmitate, 2-methylpropanoic acid, 3-methylthiopropanoic acid, myristic acid, nonanoic acid, octanoic acid (octoic acid), oleic acid, palmitic acid, potassium, scopoletin, undecanoic acid, (Z,Z)-2,5-undecadien-1-ol, and vomifol; (from the roots): anthraquinones, asperuloside (rubichloric acid), damnacanthal, glycosides, morindadiol, morindine, morindone, mucilaginous matter, nor-damnacanthal, rubiadin, rubiadin monomethyl ether, resins, soranjidiol, sterols, and trihydroxymethyl anthraquinone-monomethyl ether; (from the root bark): alizarin, chlororubin, glycosides (pentose, hexose), morindadiol, morindanigrine, morindine, morindone, resinous matter, rubiadin monomethyl ether, and soranjidiol; (from the wood): anthragallol-2,3-dimethylether; (from the tissue culture): damnacanthal, lucidin, lucidin-3-primeveroside, and morindone-6beta-primeveroside; (from the plant): alizarin, alizarin-alpha-methyl ether, anthraquinones, asperuloside, hexanoic acid, morindadiol, morindone, morindogenin, octanoic acid, and ursolic acid.

Recently, as mentioned, many health benefits have been discovered stemming from the use of products containing *Morinda citrifolia*. One benefit of *Morinda citrifolia* is found in its ability to isolate and produce Xeronine, which is a relatively small alkaloid physiologically active within the body. Xeronine occurs in practically all healthy cells of plants, animals and microorganisms. Even though *Morinda citrifolia* has a negligible amount of free Xeronine, it contains appreciable amounts of the precursor of Xeronine, called Proxeronine. Further, *Morinda citrifolia* contains the inactive form of the enzyme Proxeronase which releases Xeronine from Proxeronine. A paper entitled, "The Pharmacologically Active Ingredient of Noni" by R. M. Heinicke of the University of Hawaii, indicates that *Morinda citrifolia* is "the best raw material to use for the isolation of xeronine," because of the building blocks of Proxeronine and Proxeronase. These building blocks aid in the isolation and production of Xeronine within the body. The function of the essential nutrient Xeronine is fourfold.

First, Xeronine serves to activate dormant enzymes found in the small intestines. These enzymes are critical to efficient digestion, calm nerves, and overall physical and emotional energy.

Second, Xeronine protects and keeps the shape and suppleness of protein molecules so that they may be able to pass through the cell walls and be used to form healthy tissue. Without these nutrients going into the cell, the cell cannot perform its job efficiently. Without Proxeronine to produce Xeronine our cells, and subsequently the body, suffer.

Third, Xeronine assists in enlarging the membrane pores of the cells. This enlargement allows for larger chains of peptides (amino acids or proteins) to be admitted into the cell. If these chains are not used they become waste.

Fourth, Xeronine, which is made from Proxeronine, assists in enlarging the pores to allow better absorption of nutrients.

Each tissue has cells which contain proteins which have receptor sites for the absorption of Xeronine. Certain of these proteins are the inert forms of enzymes which require absorbed Xeronine to become active. Thus Xeronine, by converting the body's procollagenase system into a specific protease, quickly and safely removes the dead tissue from skin. Other proteins become potential receptor sites for hormones after they react with Xeronine. Thus the action of *Morinda citrifolia* in making a person feel well is probably caused by Xeronine converting certain brain receptor proteins into active sites for the absorption of the endorphin, the well being hormones. Other proteins form pores through membranes in the intestines, the blood vessels and other body organs. Absorbing Xeronine on these proteins changes the shape of the pores and thus affects the passage of molecules through the membranes.

Because of its many benefits, *Morinda citrifolia* has been known to provide a number of anecdotal effects in individuals having cancer, arthritis, diabetes, indigestion, malignancies, broken bones, high blood pressure, diabetes, pain, infection, asthma, toothaches, blemishes, immune system failure, and others.

The compositions containing *Morinda citrifolia* may be in a form suitable for oral use, for example, as tablets, or lozenges, aqueous or oily suspensions, dispersible powders or granules, emulsions, syrups or elixirs. Compositions intended for oral use may be prepared according to any method known in the art for the manufacture of *Morinda citrifolia* compositions and such compositions may contain one or more agents selected from the group consisting of sweetening agents, flavoring agents, coloring agents and preserving agents. Tablets contain *Morinda citrifolia* in admixture with non-toxic pharmaceutically acceptable excipients which are suitable for the manufacture of tablets. These excipients may be for example, inert diluents, granulating and disintegrating agents, binding agents, and lubricating agents. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed.

Aqueous suspensions contain the *Morinda citrifolia* in admixture with excipients suitable for the manufacture of aqueous suspensions. Such excipients are suspending agents, for example, sodium carboxymethyl-cellulose, methylcellulose, hydroxy-propylmethycellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethylene-oxycetanol, or condensation products of ethylene oxide with partial esters derived from fatty acids and a hexitol such as polyoxyethylene sorbitor monooleate, or condensation products of ethylene oxide with partial esters derived from fatty acids and hexitol anhydrides, for example polyethylene sorbitan monooleate.

In still another exemplary embodiment, a preferred embodiment, the processed *Morinda citrifolia* product may comprise an extract from the leaves of the Indian Mulberry plant in the form of a processed *Morinda citrifolia* leaf hot water extract, a processed *Morinda citrifolia* leaf ethanol extract, and a processed *Morinda citrifolia* leaf steam distillation extract. The process used to obtain each of these processed *Morinda citrifolia* leaf extracts is described in greater detail below.

Favorably, this invention provides a method of diabetes with a *Morinda citrifolia*-based formulation without any significant tendency to cause undesirable side effects.

Treatment Methods and Preventative Effects of *Morinda Citrifolia* on Diabetes

The present invention features a unique formulation and method of administering the same to treat diabetes, or rather advances treatment of diabetes by providing a naturaceutical composition or treatment formulated with one or more processed *Morinda citrifolia* products derived from the Indian Mulberry plant. The *Morinda citrifolia* product is incorporated into various carriers or naturaceutical compositions suitable for in vivo treatment of a patient. For instance, the naturaceutical formulation may be ingested orally, introduced via an intravenous injection or feeding system, or otherwise internalized as is appropriate and directed.

As mentioned, diabetes results from high levels of blood glucose resulting from defects in insulin secretion, insulin action, or both. It is characterized as a progressive breakdown in normal insulin-related usage of glucose. In order to function properly, the body's use of glucose must comprise a balanced output of insulin from the pancreas to transport glucose effectively to other organs and tissues for storage. Any insulin imbalance or loss of sensitivity can cause a chronic overabundance of glucose leading to diabetes.

According to the present invention, internalizing the naturaceutical formulation comprising one or more processed *Morinda citrifolia* products, as well as other ingredients if desired, serves to treat diabetes by normalizing glucose and insulin levels and their activities within the body.

The naturaceutical composition of the present invention comprises one or more of a processed *Morinda citrifolia* product present in an amount by weight between about 0.01 and 100 percent by weight, and preferably between 0.01 and 95 percent by weight. Several exemplary embodiments of formulations are provided below. However, these are only intended to be exemplary as one ordinarily skilled in the art will recognize other formulations or compositions comprising the processed *Morinda citrifolia* product.

The processed *Morinda citrifolia* product is the active ingredient or contains one or more active ingredients, such as Quercetin and Rutin, and others, for treating and relieving existing diabetes, as well as reducing the potential of developing diabetes in the future. Active ingredients may be extracted out using various alcohol or alcohol-based solutions, such as methanol, ethanol, and ethyl acetate, and other alcohol-based derivatives using any known process in the art. The active ingredients of Quercetin and Rutin are present in amounts by weight ranging from 0.01–10 percent of the total formulation or composition. These amounts may be concentrated as well into a more potent concentration in which they are present in amounts ranging from 10 to 100 percent.

The naturaceutical composition comprising *Morinda citrifolia* may be prepared using any known means in the art. In addition, since the naturaceutical composition will most likely be consumed orally, it may contain one or more agents selected from the group consisting of sweetening agents, flavoring agents, coloring agents, preserving agents, and other medicinal agents as directed.

The present invention further features a method of administering a naturaceutical composition to a mammal for the treatment and relief of diabetes and to help prevent or reduce the likelihood of contracting diabetes in the future. The method for administering a naturaceutical, or the method for treating a diabetes, comprises the steps of (a) formulating a naturaceutical composition comprising in part a processed *Morinda citrifolia* product present in an amount between about 0.01 and 95 percent by weight, wherein the composition also comprises a carrier, such as water or purified water, and other natural or artificial ingredients; (b) introducing the naturaceutical composition into the body, such that the processed *Morinda citrifolia* product is sufficiently internalized; (c) repeating the above steps as often as necessary to provide an effective amount of the processed *Morinda citrifolia* product to the body of the patient to positively affect several diabetes related conditions. Specifically, the processed *Morinda citrifolia* products function to inhibit absorption of glucose, reduce blood glucose levels, balancing insulin output and glucose transfer, accelerating glucose metabolism, and overall, increasing the body's tolerance of glucose.

The step of introducing the naturaceutical composition into the body comprises one of ingesting the composition orally. Ingesting the naturaceutical orally means the naturaceutical composition may be formulated as a liquid, gel, solid, or some other type that would allow the composition to be quickly digested and concentrated within the body. It is important to note that the step of administering the naturaceutical composition should be carried out in an effective manner so that the greatest concentration of naturaceutical composition, and particularly the processed *Morinda citrifolia* product, is internalized and absorbed into the patient's body. For the naturaceutical composition to take effect, it must be sufficiently internalized. Once sufficiently internalized, it may then begin to function to treat diabetes and its associated conditions or symptoms, and to reduce potential of being diagnosed with diabetes in the future. Specifically, once internalized, the *Morinda citrifolia* product may function to balance insulin output and glucose transfer, reduce glucose synthesis, accelerate glucose metabolism in the body, inhibit glucose absorption, and improve glucose tolerance. In one embodiment, the naturaceutical composition is administered by taking between 1 teaspoon and 2 oz., and preferably 2 oz., of the naturaceutical composition every two hours each day, or at least twice a day. Also, the naturaceutical composition is to be taken on an empty stomach, meaning at a period of time at least two hours prior to consumption of any food or drink. Following this, the naturaceutical composition is sufficiently allowed to absorb into the tissues of the body. Of course, one ordinarily skilled in the art will recognize that the amount of composition and frequency of use may vary from individual to individual.

In addition, the step of administering the naturaceutical composition may include injecting the composition into the body using an intravenous pump. This technique is advantageous as it would allow the composition to be localized in the area where it would have the most effect, or the area that would provide for the greatest concentration of the naturaceutical composition.

The treatment of diabetes by normalizing glucose insulin activity and levels results from the affect on the body of the processed *Morinda citrifolia* products, and/or the active ingredients found therein, namely Quercetin, Rutin, Xeronine, and the building blocks to Xeronine-Proxeronase and Proxeronine.

The following tables illustrate or represent some of the preferred formulations or compositions of the naturaceutical as contemplated by the present invention. It should be noted that these formulations are only intended as exemplary embodiments and are not to be construed as limiting in any way.

| Formulation One | |
| --- | --- |
| Ingredients | Percent by Weight |
| *Morinda citrifolia* leaf hot water extract | 0.1–80% |
| Water | 20–99.9% |

| Formulation Two | |
| --- | --- |
| Ingredients | Percent by Weight |
| *Morinda citrifolia* leaf ethanol extract | 0.1–100% |

| Formulation Three | |
| --- | --- |
| Ingredients | Percent by Weight |
| *Morinda citrifolia* leaf steam distillation extract | 0.1–100% |

Formulation Four

| Ingredients | Percent by Weight |
| --- | --- |
| *Morinda citrifolia* fruit juice or puree juice | 90–99.9% |
| *Morinda citrifolia* leaf water extract | 0.1–10% |

Formulation Five

| Ingredients | Percent by Weight |
| --- | --- |
| *Morinda citrifolia* fruit juice or puree juice | 90–99.9% |
| *Morinda citrifolia* leaf ethanol extract | 0.1–10% |

Formulation Six

| Ingredients | Percent by Weight |
| --- | --- |
| *Morinda citrifolia* fruit juice or puree juice | 90–99.9% |
| *Morinda citrifolia* leaf steam distillation extract | 0.1–10% |

Formulation Seven

| Ingredients | Percent by Weight |
| --- | --- |
| *Morinda citrifolia* leaf extract (water, ethanol, or steam distillation) | 0.1–10% |
| *Morinda citrifolia* fruit or puree juice or fruit/puree juice concentrate | 90–99.9% |
| Dietary supplement or food product | 90–99.9% |

Formulation Eight

| Ingredients | Percent by Weight |
| --- | --- |
| *Morinda citrifolia* puree juice or fruit juice | 100% |

Formulation Nine

| Ingredients | Percent by Weight |
| --- | --- |
| *Morinda citrifolia* fruit juice | 85–99.99% |
| Water | 0.1–15% |

Formulation Ten

| Ingredients | Percent by Weight |
| --- | --- |
| *Morinda citrifolia* fruit juice | 85–99.99% |
| non-*Morinda citrifolia*-based fruit juices | 0.1–15% |

Formulation Eleven

| Ingredients | Percent by Weight |
| --- | --- |
| *Morinda citrifolia* fruit juice | 50–90% |
| Water | 0.1–50% |
| non-*Morinda citrifolia*-based fruit juices | 0.1–30% |

Formulation Twelve

| Ingredients | Percent by Weight |
| --- | --- |
| *Morinda citrifolia* puree juice | 85–99.9% |
| Water | 0.1–15% |

Formulation Thirteen

| Ingredients | Percent by Weight |
| --- | --- |
| *Morinda citrifolia* puree juice | 85–99.9% |
| non-*Morinda citrifolia*-based fruit juices | 0.1–15% |

Formulation Fourteen

| Ingredients | Percent by Weight |
| --- | --- |
| *Morinda citrifolia* puree juice | 50–90% |
| Water | 0.1–50% |
| non-*Morinda citrifolia*-based fruit juices | 0.1–30% |

Formulation Fifteen

| Ingredients | Percent by Weight |
| --- | --- |
| *Morinda citrifolia* dietary fiber | 0.1–30% |
| Water | 1–99.9% |
| non-*Morinda citrifolia*-based fruit juices | 1–99.9% |

Formulation Sixteen

| Ingredients | Percent by Weight |
| --- | --- |
| *Morinda citrifolia* dietary fiber | 0.1–30% |
| Water | 1–99.9% |
| *Morinda citrifolia* fruit juice or puree juice | 1–99.9% |

Formulation Seventeen

| Ingredients | Percent by Weight |
| --- | --- |
| *Morinda citrifolia* puree juice concentrate or fruit juice concentrate | 100% |

Formulation Eighteen

| Ingredients | Percent by Weight |
| --- | --- |
| *Morinda citrifolia* fruit juice concentrate or puree juice concentrate | 85–99.99% |
| Water | 0.1–15% |

In an exemplary embodiment or method, a person suffering from diabetes, or a person desiring to prevent the onset of diabetes, as described above takes at least one ounce of a naturaceutical formulation comprising the ingredients in one of Formulations 1–7 in the morning on an empty stomach, and at least one ounce at night on an empty stomach, just prior to retiring to bed.

In another exemplary method, a person suffering from diabetes, or a person desiring to prevent the onset of diabetes, as described above takes at least one ounce of a naturaceutical formulation as identified in Formulation Seven in the morning on an empty stomach, and at least one ounce at night on an empty stomach, just prior to retiring to bed. In one example, which is not meant to be limiting in any way, the beneficial *Morinda Citrifolia* is processed into Tahitian Noni® juice as manufactured by *Morinda*, Incorporated of Orem, Utah.

Other similar methods of treating diabetes using each of the Formulations identified above are contemplated by the present invention. For example, any of the ingredients identified may be combined in the naturaceutical formulation described herein in any effective combination and in any effective concentration. In addition, the naturaceutical formulations described and inherently provided for herein may be introduced to the body using any known means in the art, such as orally, intravenously, transdermally, and systemically.

The present invention further features taking a diabetes medication, such as a prescription pharmaceutical, concurrently with the naturaceutical formulation. Diabetes medications used to treat the disease are well known in the art and to one ordinarily skilled in the art, and thus are not specifically recited herein.

Taking or administering the naturaceutical formulation comprising one form or another of a processed *Morinda citrifolia* product as taught and described herein functions to enhance the relief potential for the patient by increasing or enhancing the efficacy of the diabetes medication, as well as providing the same benefits and advantages to the patient that are obtained directly from the naturaceutical formulation.

Taking one form or another of a processed *Morinda citrifolia* product as taught herein increases the efficacy of doctor prescribed diabetes medications. The processed *Morinda citrifolia* products described herein are very active against cytochrome enzymes, which are responsible for the breaking down or metabolizing of medications. As such, the present invention processed *Morinda citrifolia* products prevent or significantly reduce the breaking down or metabolizing of diabetes medications by inhibiting the drug breakdown functions of the cytochrome enzymes. As a result, the diabetes medications are allowed to be in the body much longer, which naturally allows them to be more effective.

The processed *Morinda citrifolia* products have been shown to be effective for treating diabetes of all types, including Type I, Type II, and Type III. However, the present invention is found to be most effective against Type II diabetes.

Since diabetes is linked to many factors, the present invention naturaceutical comprising one or more processed *Morinda citrifolia* products is believed to be effective in reducing the likelihood of these factors contributing to the contraction of diabetes. Also, the processed *Morinda citrifolia* products are effective in treating pre-existing conditions of diabetes by targeting these factors. In reference to many of these contributing or causing factors, the present invention therefore features a method for balancing insulin output and glucose transfer, a method for reducing glucose synthesis in the liver, a method for accelerating glucose metabolism in the body of a mammal, a method for inhibiting glucose absorption, particularly in the digestive tract, of a mammal, and a method for improving glucose tolerance in the body of a mammal. Each of these methods comprises the prophylactic administration of a naturaceutical formulation to a patient in a safe, pre-determined amount (e.g., at least one teaspoon and preferably two ounces), for a safe, pre-determined frequency (e.g., twice daily on an empty stomach), and for a safe, pre-determined duration of time (e.g., each day), wherein the naturaceutical formulation comprising one or more processed *Morinda citrifolia* products present in an amount by weight as identified above.

In one exemplary, and preferred embodiment, the processed *Morinda citrifolia* product comprises one of a processed *Morinda citrifolia* leaf hot water, ethanol, or steam distilled extract as obtained according to the process described herein. Of course, the naturaceutical formulation may comprise other ingredients, such as water, other food products or food supplements, dietary supplements, flavorings, etc. and may also be embodied in any form, including a liquid, gel, capsule, lozenge, etc.

The following examples set forth and present the effects of *Morinda citrifolia* on both pre-existing diabetes conditions, as well as the preventative effects of *Morinda citrifolia* against the onset of or contracting diabetes. These examples are not intended to be limiting in any way, but are merely illustrative of the beneficial, advantageous, and remedial effects of *Morinda citrifolia* on diabetes. Other non-limiting examples of the present invention are described below.

EXAMPLE ONE

In the present example, a patient experiencing and diagnosed with Type II diabetes desires to treat the disease with a non-prescription, over-the-counter remedy or preparation. Thus, to treat the diabetes, an individual is given an identified, prescribed amount of a naturaccutical composition to consume orally, wherein the naturaceutical comprises a processed *Morinda citrifolia* leaf extract (e.g., hot water leaf extract, ethanol leaf extract, or steam distilled leaf extract) present in an amount between 0.1 and 50 percent by weight, with water or other juices (such as processed *Morinda citrifolia* fruit or puree juice, grape juice, etc.) comprising the remainder of the naturaceutical formulation. The naturaceutical is administered in a safe, pre-determined amount, namely at least one ounce, and is administered intermittently a safe, pre-determined number of times, namely twice a day, for a safe, pre-determined amount of time, namely each day. Administration of the naturaceutical formulation effectively functions to normalize insulin production, increase glucose metabolism, inhibit glucose absorption, and reduce glucose synthesis in the liver. The *Morinda citrifolia*-based naturaceutical is consumed by the patient on an empty stomach.

EXAMPLE TWO

In an actual example the medical benefit of a processed *Morinda Citrifolia* product was tested. Processed *Morinda Citrifolia* leaf hot water and alcohol extracts were studied using a rat model with streptozotocine induced diabetes. The *Morinda Citrifolia* leaf extracts were harvested from *Morinda Citrifolia* leafs which were frozen, defrosted, dried, and chopped, wherein the extract was formed using demonized distilled hot water. The extract was first tested for acute toxicity, which was found negative.

A rat model was selected based on the reasoning that high blood glucose shown in non-insulin dependent diabetes is associated with secretory disorders of pancreatic insulin, and/or a reduction of glucose production in the liver and/or an intinuation of insulin reaction to glucose uptake at peripheral tissues in the muscles, fatty tissues and other tissues of the body.

Given that the *Morinda Citrifolia* products are effectively providing a therapeutic effect for people suffering from type II diabetes, the results of this example show that there is no toxic effect from the consumption of a *Morinda Citrifolia* leaf extract. The results also indicated that there is no evidence of toxicity found in the animals. No animals died during the test and no behavioral changes were observed in any of the animals. Additionally, there were no signs of athrocytosis, no significant weight gain observed in the test group as compared to control groups, and no observed abnormality in the inner organs. Based on the above results, there appeared to be no toxicity related to the use of the *Morinda Citrifolia* leaf extract on animals with streptozotocine induced diabetes.

EXAMPLE THREE

Various medicinal efficacies of the leaves from the Indian Mulberry plant are set forth herein, particularly diabetes improvement efficacy. In the present test, the object was to conduct a comparative study of anti-diabetic functions of various *Morinda citrifolia* leaf extracts, using fasting-time sugar level as markers.

First, frozen *Morinda citrifolia* leaves were defrosted and chopped into small pieces at the room temperature. Distilled water, five times the volume of the chopped leaves, was added and hot water extraction was conducted for an hour. Then the solids in the solution were removed by centrifugation and the supernatant obtained was freeze-dried as a processed *Morinda citrifolia* leaf hot water extract.

Second, frozen *Morinda citrifolia* leaves were defrosted and chopped into small pieces at the room temperature. Distilled water, five times the volume of the chopped leaves, was added, and agitated at 40° C. while extraction was conducted for one hour. After removing solid objects, ethanol was removed under decreasing pressure (rotary evaporator). Solids produced were removed with a fiberglass filter. The resulting supernatant was freeze dried as a processed *Morinda citrifolia* leaf ethanol extract.

Third, frozen *Morinda citrifolia* leaves were defrosted and chopped into small pieces at room temperatures. The chopped leaves were steam distilled using a sub-critical steam distillation apparatus. Then the solids in the solution were removed by centrifugation and the supernatant obtained was freeze dried as a processed *Morinda citrifolia* leaf steam distilled extract. Other methods or procedures not specifically recited herein may be used to extract out the active ingredients found in the processed *Morinda citrifolia* leaf extracts, as will be apparent to one ordinarily skilled in the art. Therefore, the methods and procedures that are specifically recited herein are not intended to be limiting in any way.

In regards to the feeding method, Wistar-type, five-week-old male rats (weight 100±10 g), five per group were used. Rats were fed under conditions of 25° C. room temperature, 50% humidity and light-dark cycle of 12 hours (8:00~20: 00). To introduce the processed *Morinda citrifolia* leaf extracts into the rats' bodies, the rats were administered the aforementioned freeze-dried material by adding it to their drinking water in such a manner that the material became 0, 15, 30, 60, 150, and 300 mg/kg body weight/day. The drinking water was made freely available to the animals.

In regards to the testing, streptozotocin (STZ) was dissolved in 0.1 M citric acid buffer (pH 4) to form 35 mg/kg weight solution, and the solution was injected in the abdominal cavity immediately. Three weeks later, after verifying that blood sugar level was sufficiently high, the test material was administered. Each week, blood was taken from the animal and serum was obtained using a normal method. A Determiner GL-E was utilized for measurement of blood sugar levels.

Elapsed time change of blood sugar level was determined. Based on the results obtained, each of the processed *Morinda citrifolia* leaf extracts were determined to have a significant effect on type II diabetes.

When each *Morinda citrifolia* leaf extract was orally administered to rats with STZ-induced type II diabetes (non insulin dependent diabetes, NIDDM), the blood sugar level declined. The rate of decline was the highest in the processed *Morinda citrifolia* leaf ethanol extract, followed by the processed *Morinda citrifolia* leaf steam distilled extract and processed *Morinda citrifolia* leaf hot water extracts. However, no significant difference was found between the processed *Morinda citrifolia* leaf ethanol extract and processed *Morinda citrifolia* leaf steam distilled extract. Moreover, rate of decline in blood sugar level increased proportionally to the amount administered, but no remarkable efficacy was found when the administration amount was higher than 160 mg/kg weight/day. The blood sugar level decline rate of the group in the fourth week to which the processed *Morinda citrifolia* leaf ethanol extract was given with 300 mg/kg weight/day was about 12% compared to the group without administration of the material. Likewise, the rate of the group to which the processed *Morinda citrifolia* leaf steam distilled extract was administered with 300 mg/kg weight/day was about 11% and the rate of the group to which the processed *Morinda citrifolia* leaf hot water extract was administered with 300 mg/kg weight/day was about 7%.

From the results above, it is concluded that processed *Morinda citrifolia* leaf extracts have efficacy to control, to some degree, rises in blood sugar level caused by STZ-induced type II diabetes (insulin non-dependent diabetes, NIDDM) when administered orally. In recent years, more people have expressed the view that the STZ-induced experimental diabetes model, though in principle it is a type I model, may be used as a type II model, particularly in fast screening applications. Hence, a decision was made to use the STZ-induced diabetes model in the present test.

Because processed *Morinda citrifolia* leaf extracts were found during preliminary glucose load tests to have a tendency to block glucose absorption, the anti-diabetes function of *Morinda citrifolia* is thought to be absorption control. However, because the STZ-induced experimental diabetes model mouse resembles type I diabetes which has dependency on insulin, further study is necessary to carefully examine blood sugar level, hemoglobin, A1C, GLUT-4 receptor conditions and insulin resistance using the KKAy mouse (natural type II diabetes model mouse).

EXAMPLE FOUR

In another actual example, in order to study the effects of *Morinda Citrifolia* extract on non-insulin dependent diabetes (Type II), as well as administration of food samples containing processed *Morinda Citrifolia* leaf extracts (either hot water, ethanol, or steam distilled as described above), a test of Type II diabetes patients was undertaken. Volunteers currently receiving treatment for Type II diabetes were selected. The subjects were men and women in their forties and fifties and were randomly divided into groups. A total of two test food groups using processed *Morinda Citrifolia* leaf extracts were organized.

In one group, 0.1 grams of *Morinda Citrifolia* leaf extracts were mixed into food samples. In another group, 0.2 grams of *Morinda Citrifolia* leaf extracts were mixed in the food samples, and in the third group, 0.75 grams of *Morinda Citrifolia* leaf extracts were mixed into food substances. In a fourth group, food substances were prepared by mixing in 0.75 grams of a *Morinda Citrifolia* leaf extract after removing TS extract. Three patients were assigned to each food group.

Packets containing two grams of the *Morinda Citrifolia* leaf extract mixed in powder form were laminate coated and sealed in aluminum. Packs were given to volunteers under physician's direction. The physician was asked to advise the volunteers to refrain from taking the medication glibenclamide if a patient was currently using the medication. Use of a glycosidase inhibitor (such as Glucobai), was prohibited.

Each volunteer was asked to take the food material in a tea-like substance twice a day during meals. The patients were instructed to dissolve one envelope with approximately 150 ml of hot water. Blood sugar values were measured for each of the patients at least twice for each volunteer. The patients' blood sugar levels were measured between 7:00 and 8:00 am on an empty stomach using glucogye GT 1614 made by Arcly Factory KK.

The results of the study show that in the group without the TS extract a drop of approximately 4 percent was detected in the blood sugar value on an empty stomach. A drop of about 23 percent in the blood sugar value was detected when the TS extract was added. These results show that processed *Morinda citrifolia* leaf extracts provide a significant and effective treatment against diabetes, as well as a significant and effective deterrent against contracting the disease.

The present invention may be embodied in other specific forms without departing from its spirit of essential characteristics. The described embodiments are to be considered in all respects only al illustrative and not restrictive. The scope of the invention is, therefore, indicated by the appended claims, rather than by the foregoing description. All changes which come within the meaning and range of equivalency of the claims are to be embraced within their scope.

What is claimed and desired to be secured by Letters Patent is:

1. A formulation for treating diabetes comprising:
  a formulation comprising a processed *Morinda citrifolia* leaf hot water extract present in an amount by weight between about 0.1 and 50 percent;
  quercetin;
  rutin; and
  an ingredient selected from the group consisting of a combination of processed *Morinda citrifolia* products, food supplements, dietary supplements, and flavorings, wherein said quercetin is present in an amount between about 0.1 and 10 percent by weight and wherein said rutin is present in an amount between about 0.1 and 10 percent by weight.

2. The formulation of claim 1, wherein said formulation further comprises a processed *Morinda citrifolia* leaf ethanol extract present in an amount by weight between about 0.1 and 50 percent.

3. The formulation of claim 1, wherein said formulation further comprises a processed *Morinda citrifolia* leaf steam distillation extract present in an amount by weight between about 0.1 and 50 percent.

4. The formulation of claim 1, wherein said formulation further comprises *Morinda citrifolia* fruit juice.

5. The formulation of claim 1, wherein said formulation further comprises *Morinda citrifolia* puree juice.

6. The formulation of claim 1, wherein said formulation further comprises *Morinda citrifolia* puree juice concentrate.

7. The formulation of claim 1, wherein said formulation further comprises *Morinda citrifolia* fruit juice concentrate.

8. The formulation of claim 1, wherein said formulation further comprises *Morinda citrifolia* dietary fiber.

9. The formulation of claim 1, wherein said formulation is administered orally.

10. The formulation of claim 1, wherein said formulation is administered intravenously.

11. The formulation of claim 1, wherein said formulation is administered systemically.

* * * * *